(12) United States Patent
Maseeh

(10) Patent No.: US 6,721,053 B1
(45) Date of Patent: Apr. 13, 2004

(54) SYSTEM FOR HIGH RESOLUTION CHEMICAL AND BIOLOGICAL SENSING

(75) Inventor: Fariborz Maseeh, Boston, MA (US)

(73) Assignee: Corning Intellisense Corporation, Wilmington, MA (US)

( * ) Notice: Subject to any disclaimer, the term of this patent is extended or adjusted under 35 U.S.C. 154(b) by 0 days.

(21) Appl. No.: 09/314,697

(22) Filed: May 19, 1999

(51) Int. Cl.[7] .......................... G01N 21/85; G02B 6/00
(52) U.S. Cl. ........................................ 356/436; 385/12
(58) Field of Search ................................ 356/436, 246, 356/440; 385/12, 13

(56) References Cited

U.S. PATENT DOCUMENTS

| | | |
|---|---|---|
| 5,262,842 A | 11/1993 | Gauglitz et al. |
| 5,465,151 A | 11/1995 | Wybourne et al. |
| 5,644,125 A | 7/1997 | Wobschall |
| 5,663,790 A | 9/1997 | Ekstrom et al. |
| 5,858,802 A | 1/1999 | Chai-Gao et al. |
| 5,872,877 A | 2/1999 | Haavisto |

FOREIGN PATENT DOCUMENTS

| | | |
|---|---|---|
| WO | WO 98/28075 | 7/1998 |
| WO | WO 98/46981 | 10/1998 |

*Primary Examiner*—Zandra Smith
(74) *Attorney, Agent, or Firm*—Peter F. Corless; Steven M. Jensen; Edwards & Angell, LLP

(57) ABSTRACT

An MEOMS sensing chip for optically detecting and measuring substances in fluid samples is disclosed. The MEOMS sensing chip includes a system for optically sensing substances in the fluid samples and a system for delivering the fluid samples to the sensing system. The sensing system includes a two-branch channel waveguide and a plurality of ring waveguides, each branch in the two-branch waveguide being used for evanescently coupling light energy into one of the ring waveguides. The delivering system includes a plurality of micro-channels and a plurality of micro-wells, the micro-channels being used for transporting the fluid samples to the micro-wells. Each micro-well is aligned with a respective ring waveguide and is used for exposing the fluid sample contained therein to the respective ring waveguide. Characteristics related to the evanescent coupling of the light energy into the ring waveguides, e.g., resonant frequencies of the ring waveguides, are used for detecting substances in the fluid samples.

11 Claims, 4 Drawing Sheets

SYSTEM FOR HIGH RESOLUTION CHEMICAL AND BIOLOGICAL SENSING

BACKGROUND OF THE INVENTION

1. Field of the Invention

This invention relates generally to systems for performing optical sensing, and more particularly to micro-machined electrical-optical-mechanical systems for high-resolution chemical and biological sensing applications.

2. Background

Recent advances in processes for micro-machining silicon have made it possible to implement complete micro-machined electrical-optical-mechanical systems (MEOMS) on a chip. For example, MEOMS have recently been developed that incorporate sensors for detecting substances and measuring related physical properties. An important advantage of such MEOMS is the ability to place interfaces, sensors, and signal processing circuitry on the same silicon substrate, thereby making these systems high speed, portable, and relatively low cost.

A traditional method of detecting chemical and biological substances and measuring related physical properties, which may be implemented as part of a MEOMS, involves an optical technique known as evanescent wave surface detection. Generally, evanescent wave surface detection includes applying a fluid sample to the surface of a waveguide. Frequently, the waveguide surface is coated with a chemically sensitive layer and the fluid sample is allowed to react with this layer. Next, light is coupled into the waveguide, and the light propagating through the waveguide causes evanescent wave fields to be produced that reach out into the fluid sample on the waveguide surface. Because the fluid sample applied to the waveguide surface changes the effective index of refraction of the waveguide, the light propagating through the waveguide undergoes a shift in phase. Accordingly, the fluid sample on the waveguide surface can be detected and properties relating to the fluid sample can be measured by measuring the phase shift of the light coupled out of the waveguide.

One optical technique for detecting chemical and biological substances that uses evanescent wave surface detection is disclosed in U.S. Pat. No. 5,120,131 issued Jun. 9, 1992 to Lukosz. That patent discloses a technique that includes applying a fluid sample to a waveguide surface and then coupling light into the waveguide, thereby causing evanescent wave fields to reach out into the fluid sample. Specifically, the light coupled into the waveguide is polarized so that it propagates through the waveguide as two mutually coherent and orthogonally polarized modes. This is because the penetration depths of the evanescent wave fields corresponding to the two modes are different, thereby causing the modes propagating through the waveguide to undergo different amounts of phase shift. The fluid sample on the waveguide surface is therefore detected and its properties are measured by measuring differences in the phase shifts, $\Delta\Phi$, for the two orthogonal modes.

Although this optical technique has been successfully used for detecting chemical and biological substances and measuring related physical properties, it has some drawbacks. For example, the phase difference of the two orthogonal modes can at best be determined with a resolution of $\delta(\Delta\Phi) \leq 2\pi/1000$, which is generally not good enough for detecting extremely small chemical and biological substances in the fluid sample. Biochemical and environmental factors such as non-specific binding and temperature variation in the fluid sample further limit the resolution of this optical technique.

Another optical technique that uses evanescent wave surface detection is disclosed in U.S. Pat. No. 5,262,842 issued Nov. 16, 1993 to Gauglitz et. al. That patent discloses an integrated optical Mach-Zehnder interferometer fabricated on a substrate. The interferometer includes a single mode waveguide structure for bifurcating a beam of light into two separate optical paths, which include a measurement path and a comparison path. The surface of the measurement path can be coated with a chemically sensitive layer and a fluid sample allowed to react with this layer. After propagating through the measurement and the comparison paths, the bifurcated light beams are then recombined. Because the chemically sensitive layer changes the index of refraction of the measurement path, the light beam propagating within the measurement path experiences a phase shift. As a result, interference between the two light beams can be measured in the recombined beam. Significantly, this measured interference is proportional to the quantity of chemical or biological substance in the fluid sample.

Although this optical technique including a measurement path and a comparison path has the advantage of effectively canceling out non-specific binding and temperature variation in the fluid sample, it also has drawbacks in that the resolution of the technique is generally insufficient for detecting extremely small chemical and biological substances in the fluid sample.

Not only is it desirable to have a MEOMS with high resolution sensors for detecting extremely small chemical and biological substances in fluid samples, but it is also desirable to have a MEOMS with structure that supports the testing of extremely small quantities of fluid samples. One such structure is disclosed in International Publication WO 98/28075 published Jul. 2, 1998 to Imaging Research Inc., St. Catharines, Ontario, Calif. That publication discloses a micro-well plate designed for use in imaging systems for imaging of fluorescent, chemiluminescent, bioluminescent, and colorimetric assays. Specifically, the publication discloses structure for optimizing the optical properties of the micro-wells, which are designed to hold extremely small quantities of fluid sample.

International Publication WO 98/46981 published Oct. 22, 1998 to LJL Biosystems, Sunnyvale, Calif., USA, discloses another micro-well plate design that further reduces the quantity of fluid sample required for successful imaging.

However, neither International Publication WO 98/28075 nor WO 98/46981 disclose structure for controlling the transfer of extremely small quantities of fluid sample into and out of the micro-wells. We have recognized that a practical MEOMS incorporating high-resolution chemical and biological sensors must include such structure.

It would therefore be desirable to have a MEOMS for chemical and biological sensing applications. Such a MEOMS would include high-resolution chemical and biological sensors that are capable of detecting extremely small chemical and biological substances in a fluid sample. It would also be desirable to have a MEOMS for chemical and biological sensing applications that includes structure for holding extremely small quantities of the fluid sample and for controlling the transfer of the fluid sample into and out of the MEOMS.

SUMMARY OF THE INVENTION

The foregoing drawbacks of the prior art have been overcome by an MEOMS sensing chip according to the present invention. In a preferred embodiment, the MEOMS sensing chip includes a system for optically sensing substances in fluid samples and a system for delivering the fluid samples to the sensing system, wherein the sensing system includes at least one two-branch waveguide and a plurality of ring waveguides, each branch of the two-branch waveguide being used for coupling light energy into one of the plurality of ring waveguides, wherein the delivering system includes a plurality of micro-channels and a plurality of micro-wells, the micro-channels being used for transporting the fluid samples to the micro-wells, each micro-well being aligned with a respective ring waveguide and being used for exposing the fluid sample therein to the respective ring waveguide, and wherein characteristics related to the coupling of the light energy into the plurality of ring waveguides are used for detecting substances in the fluid samples.

In another embodiment, a device for optically sensing substances in fluid samples includes a first channel waveguide for coupling light energy into a first ring waveguide, the first ring waveguide having a test sample applied to a surface thereof, a second channel waveguide for coupling light energy into a second ring waveguide, the second ring waveguide having a reference sample applied to a surface thereof; a laser for injecting light into the first and the second channel waveguides; and, at least one detector for measuring the intensities of light coupled out of the first and the second channel waveguides, wherein the intensity measurements are used for sensing substances in the test sample relative to the reference sample.

In still another embodiment, a method for optically sensing substances in fluid samples includes exposing a test sample to a first ring waveguide; injecting a light beam into a first channel waveguide, thereby coupling at least a portion of the light beam energy into the first ring waveguide; and, detecting the intensity of a remaining portion of the light beam energy coupled out of the first channel waveguide, wherein the detected energy is indicative of the presence of a substance in the test sample.

Other aspects of the invention are disclosed infra.

DETAILED DESCRIPTION OF THE INVENTION

Figure 1A:
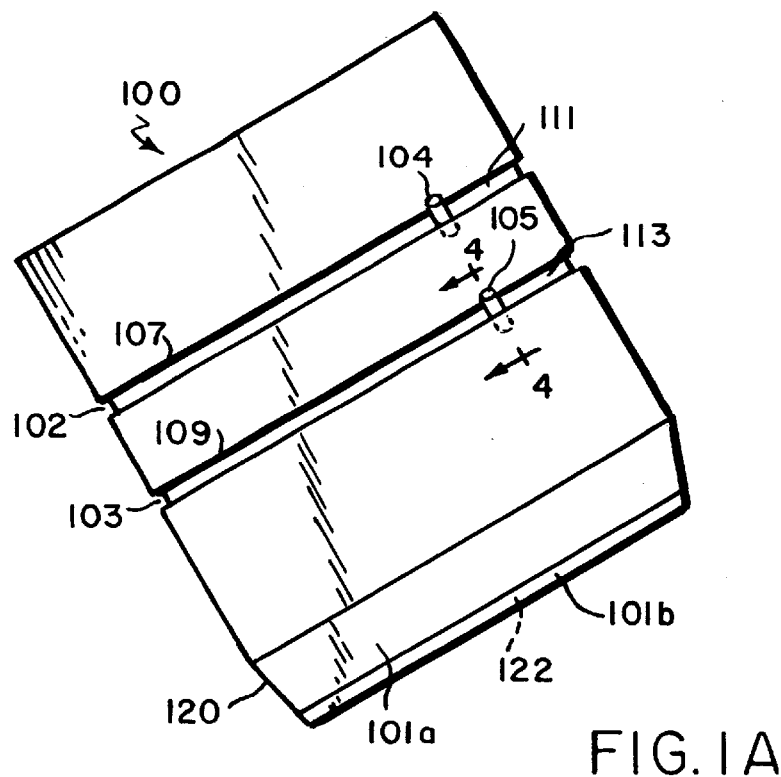
FIG. 1A is a perspective view of a MEOMS sensing chip in accordance with the present invention, showing a top surface including a micro-fluidic module in accordance with the present invention.
Figure 1B:
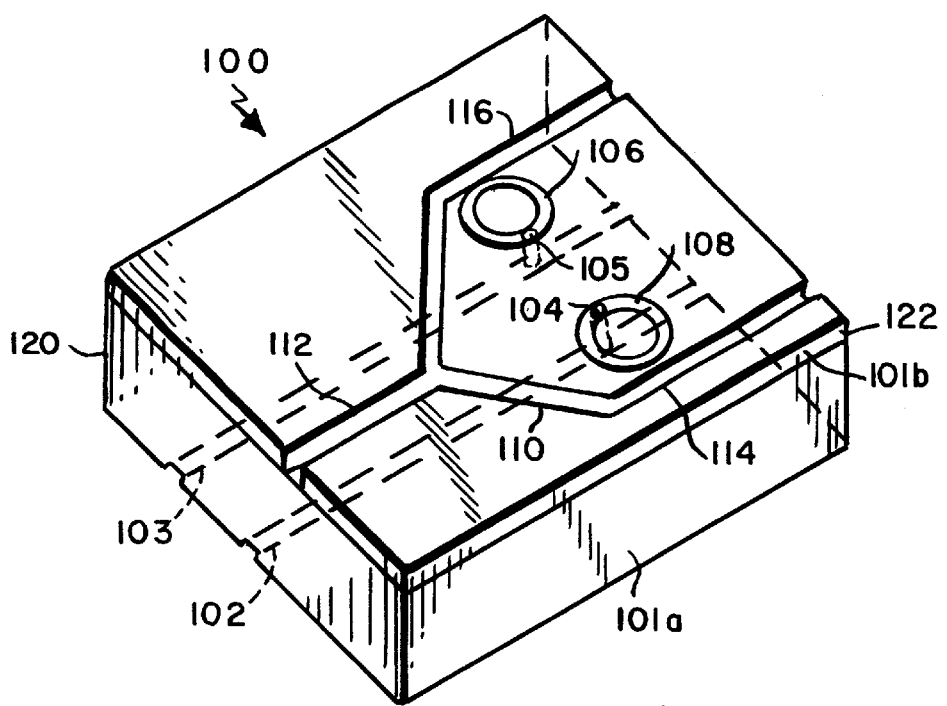
FIG. 1B is a perspective view of the MEOMS sensing chip, showing a bottom surface including an optical sensing chip module in accordance with the present invention.

Referring now to the drawings, which depict preferred devices of the invention, FIGS. 1A and 1B show two perspective views of a micro-machined electrical-optical-mechanical system (MEOMS) sensing chip 100 according to the present invention. FIG. 1A shows a top surface (not numbered) of the MEOMS sensing chip 100 comprising a micro-fluidic module 120, which includes a plurality of fluidic micro-channels 102 and 103 and associated reactor wells 104 and 105. The fluidic micro-channels 102 and 103 and the reactor wells 104 and 105 are bulk micro-machined onto a planar silicon substrate 101 a using techniques that are well known to those skilled in this art.

In the illustrative embodiment shown in FIG. 1A, the micro-channels 102 and 103 have rectangular or V-shaped cross sections and surface cross sectional areas of about 100 microns. Further, the reactor wells 104 and 105 preferably have cylindrical shapes with volume sizes of 1 mm$^3$.

The MEOMS sensing chip 100 is useful for performing chemical and biological sensing of extremely small chemical and biological substances in fluid samples (not shown). Accordingly, the reactor wells 104 and 105 function as reservoirs for holding extremely small quantities of the fluid samples, e.g., hundreds of micro-liters, during testing.

Further, the fluidic micro-channel 102 includes an inlet channel 107 and an outlet channel 111. Similarly, the fluidic micro-channel 103 includes an inlet channel 109 and an outlet channel 113. Accordingly, the inlet channels 107 and 109 function as conduits for transporting the fluid samples to the reactor wells 104 and 105, respectively, for subsequent testing; and, the outlet channels 111 and 113 function as conduits for transporting the fluid samples out of the reactor wells 104 and 105, respectively, after testing is completed. The inlet channels 107 and 109 and the outlet channels 111 and 113 may be coupled to a micro-fluidic delivery system module (not shown), which controls the transport of the fluid samples into and out of the reactor wells 104 and 105. The micro-fluidic delivery system module includes micro-fabricated pumps and fluidic channels, which are structures that are known to those skilled in this art and may therefore be readily assembled.

FIG. 1B shows a bottom surface (not numbered) of the MEOMS sensing chip 100 comprising an optical sensing chip module 122 with a two-branch channel waveguide 110, which includes an input portion 112 coupled to a measurement branch 116 and a reference branch 114. The input portion 112, the measurement branch 116, and the reference branch 114 provide optical paths for beams of light propagating within the optical sensing chip module 122.

In particular, the channel waveguide 110 may have rectangular cross sectional dimensions on the order of several micrometers, typically 2 $\mu$m to 3 $\mu$m. Further, the path length from the beginning of the input portion 112 to the end of the measurement branch 116 is equal to the path length from the beginning of the input portion 112 to the end of the reference branch 114. Because the waveguide 110 of the optical sensing chip module 122 is implemented as a channel waveguide, scattering of light beams propagating within the waveguide 110 is minimized, thereby enhancing the sensitivity of the MEOMS sensing chip 100.

The optical sensing chip module 122 also includes identical, passive, ring waveguide resonators 106 and 108. The structure and operation of passive ring waveguide resonators that may be micro-fabricated-onto planar silicon substrates are described in U.S. Pat. No. 5,872,877. issued Feb. 16, 1999 to Haavisto.

In the illustrative embodiment shown in FIGS. 1A and 1B, the ring waveguide resonator 106 functions as a measuring arm, and the ring waveguide resonator 108 functions as a reference arm. Further, a portion (not numbered) of the ring waveguide resonator 106 is aligned with the reactor well 105 and a portion (not numbered) of the ring waveguide resonator 108 is aligned with the reactor well 104, wherein the ring waveguide resonators 106 and 108 and the reactor wells 105 and 104 are formed on opposed surfaces of the MEOMS sensing chip 100 (see FIG. 1B). In this way, the fluid sample held in the reactor well 105 is exposed to the ring waveguide resonator 106, and the fluid sample held in the reactor well 104 is exposed to the ring waveguide resonator 108. The structure and cooperation of the ring waveguide resonators 106 and 108 and the reactor wells 104 and 105 will be described in further detail below with reference to FIGS. 3 and 4.

For the illustrative embodiment shown in FIGS. 1A and 1B, the micro-fluidic module 120 and the optical sensing chip module 122 are fabricated on separate planar silicon substrates 101a and 101b, respectively, which are then aligned and bonded together to form the MEOMS sensing chip 100. This manner of fabricating the MEOMS sensing chip 100 has advantages in that one process optimized for bulk micro-machining silicon can be used to make the micro-fluidic module 120; and, another process optimized, for forming channel waveguides on silicon substrates can be used to make the optical sensing chip module 122.

In an alternative embodiment, the micro-fluidic module 120 and the optical sensing chip module 122 are fabricated monolithically on the same silicon substrate (not shown), with the micro-fluidic module 120 micro-machined onto one side of the substrate and the optical sensing chip module 122 formed on the opposite side of the substrate. This alternative manner of fabricating the MEOMS sensing chip 100 has advantages in that the alignment of the micro-fluidic module 120 and the optical sensing chip module 122, i.e., the alignment of the ring waveguide resonators 106 and 108 with the reactor wells 104 and 105, may be precisely performed using photolithography. However, this manner of fabricating the MEOMS sensing chip 100, e.g., concurrently fabricating the micro-fluidic module 120 and the optical sensing chip module 122 on the same silicon substrate, may result in a fabrication process with a less than optimal number of processing steps.

Nevertheless, it should be understood that the methods used for micro-machining the micro-fluidic module 120 onto the silicon substrate 101a and forming the optical sensing chip module 122 on the silicon substrate 101b are conventional and are therefore not critical to this invention.

Figure 2:
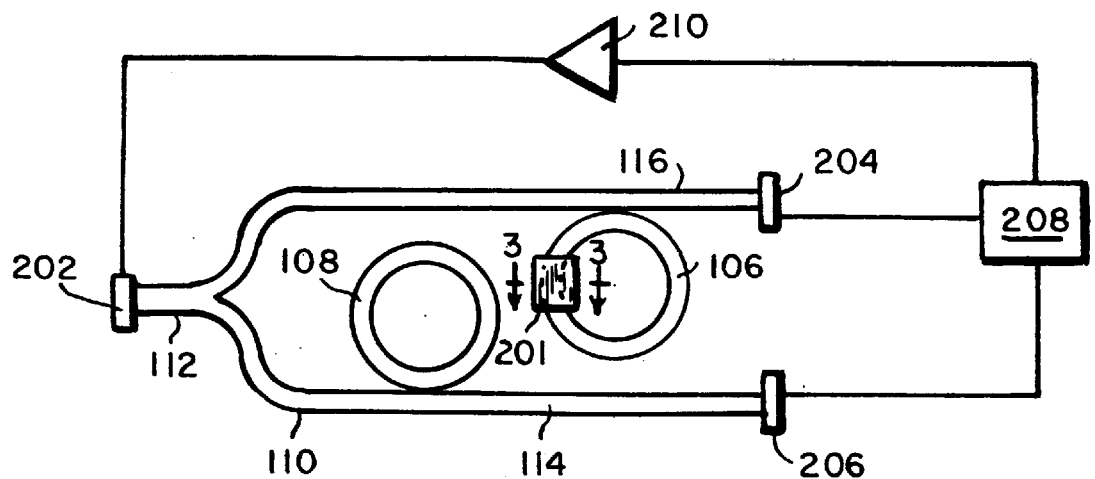
FIG. 2 is a schematic view of the optical sensing chip module in accordance with the present invention.

FIG. 2 shows a schematic view of the optical sensing chip module 122, which is coupled to a laser 202 and light intensity detectors 204 and 206. Further, the detectors 204 and 206 are coupled to a processor 208, which optionally uses a servo 210 for adjusting the frequency of light generated by the laser 202. In particular, the laser 202 injects a coherent light beam (not shown) into the input portion 112 of the channel waveguide 110, thereby causing the light beam to propagate as a single mode within the input portion 112. Any suitable integrated optical element (not shown) may be used for coupling the light beam produced by the laser 202 into the input portion 112 of the channel waveguide 110. In the preferred embodiment, the laser 202 is a gallium aluminum arsenide diode laser.

Further, any suitable integrated optical element (not shown) may be used for bifurcating the light beam propagating within the input portion 112, thereby defining a pair of respective light beams (not shown) propagating as single modes within the measurement branch 116 and the reference branch 114. The light beam propagating within the input portion 112 is preferably bifurcated so that the energies of the respective light beams propagating within the measurement and the reference branches 116 and 114 are equal.

Moreover, the energy of the light beam propagating within the measurement branch 116 is evanescently coupled into the ring waveguide resonator 106, thereby causing this light energy to propagate around the ring waveguide resonator 106 in a clockwise manner. Similarly, the energy of the light beam propagating within the reference branch 114 is evanescently coupled into the ring waveguide resonator 108, thereby causing this light energy to propagate around the ring waveguide resonator 108 in a counter clockwise manner. It should be understood that the directions of propagation of the light energies around the ring waveguide resonators 106 and 108 are not critical to this invention.

When the frequency of the light beam propagating within the measurement branch 116 equals the resonant frequency corresponding to the ring waveguide resonator 106, essentially all of the associated light beam energy will be evanescently coupled into the ring waveguide resonator 106. This means that the intensity of the light beam coupled out of the measurement branch 116 and detected by the detector 204 will fall to a minimum. Similarly, when the frequency of the light beam propagating within the reference branch 114 equals the resonant frequency corresponding to the ring waveguide resonator 108, essentially all of the energy associated with this light beam will be evanescently coupled into the ring waveguide resonator 108. The intensity of the light beam coupled out of the reference branch 114 and detected by the detector 206 will therefore fall to a minimum. Any suitable integrated optical element (not shown) may be used for coupling the light beams out of the measurement and the reference branches 116 and 114 and providing the out-coupled light beams to the detectors 204 and 206.

Generally, the relationship between the intensities, $I_{in}$ and $I^{out}$, of a light beam coupled into and out of a channel waveguide, wherein the light beam is evanescently coupled to a ring waveguide resonator with a line width, $\Gamma$, and the light frequency, $f$, is near resonance, $f_0$, may be approximated as follows:

$$I_{out}=I_{in}/[1+4/\Gamma^2(f-f_0)^2] \qquad \text{(Eq. 1)}$$

In addition, the upper surface of the ring waveguide resonator 106, which functions as a measuring arm, optionally interfaces with a chemically sensitive layer 201, which may be any suitable chemically sensitive layer known to those skilled in this art. For example, the chemically sensitive layer 201 may be a known polymer or a known biological substance that reacts with the fluid sample held in the reactor well 105, thereby changing the index of refraction of the chemically sensitive layer 201.

As mentioned above, the reactor well 105 is part of the micro-fluidic module 120, which is formed on the top surface of the MEOMS sensing chip 100. Further, the ring waveguide resonator 106 is part of the optical sensing chip module 122, which is formed on the bottom surface of the MEOMS sensing chip 100. Accordingly, the chemically sensitive layer 201 may be applied to the surface (not numbered) of the reactor well 105 that interfaces with the ring waveguide resonator 106.

Figure 3:
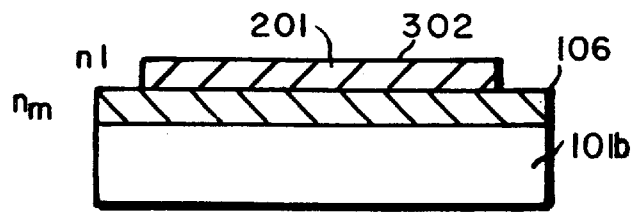
FIG. 3 is a cross sectional view of the MEOMS sensing chip of FIG. 2, taken along line 3—3.

FIG. 3 shows a cross sectional view of the optical sensing chip module 122 taken along the line 3—3 of FIG. 2. In particular, FIG. 3 shows the portion of the ring waveguide resonator 106 formed on the substrate 101b that interfaces with the chemically sensitive layer 201.

Generally, a waveguide used in optical sensing applications must have a refractive index that is greater than the refractive index of the planar substrate on which it is formed. Further, the refractive index difference must be large enough to ensure total internal reflection of light propagating within the waveguide.

For this reason, the refractive index of the channel waveguide 110 is greater than the refractive index of the substrate 101b, thereby ensuring total internal reflection of the light beams propagating within the input portion 112 and the measurement and the reference branches 116 and 114. Similarly, the refractive indices of the ring waveguide resonators 106 and 108 are greater than the refractive index of the substrate 101b, thereby ensuring total internal reflection of the light energy propagating around the ring waveguide resonators 106 and 108.

Specifically, FIG. 3 shows the optional chemically sensitive layer 201 with a refractive index, $n_l$, the ring waveguide resonator 106 (also called the measuring arm) with a refractive index, $n_m$, and the substrate 101b with a refractive index, $n_s$. Thus, in order to ensure total internal reflection of the light energy propagating around the ring waveguide resonator 106, $n_m > n_s$ and $n_m > n_l$.

Figure 4:
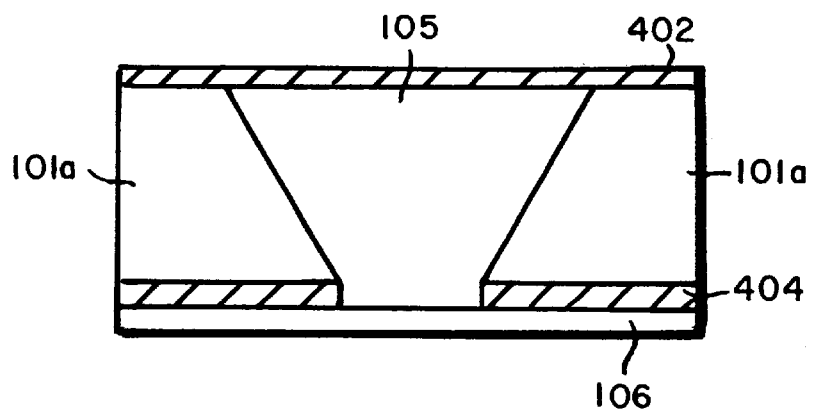
FIG. 4 is a cross sectional view of the micro-fluidic module of FIG. 1A, taken along line 4—4.

FIG. 4 shows a cross sectional view of the reactor well 105 taken along the line 4—4 of FIG. 1A. The structure of the reactor well 104 is preferably identical to the structure of the reactor well 105 and therefore will not be explicitly shown. The reactor well 105 is preferably bulk micromachined onto the silicon substrate 101a with the asymmetric cross section as shown in FIG. 4. Alternatively, the reactor well 105 may have either a tubular cross section (see FIG. 1a) or a polygonal cross section (not shown). It is expected that each of these alternative cross sections will allow maximum circulation of the fluid sample at the bottom of the reactor well 105. As mentioned above, the reactor wells 104 and 105 preferably have cylindrical shapes with volume sizes of 1 mm³.

Further, the cladding 402 hermetically seals the reactor well 105 so that no fluid sample (not shown) escapes during testing; and, the cladding 404 bonds the reactor well 105 to the optical sensing chip module 122 so that the fluid sample in the reactor well 105 is evenly exposed to the ring waveguide resonator 106. All of the inner surfaces (not numbered) of the reactor well 105 are preferably treated to have minimal interaction with chemical or biological substances in the fluid sample.

As mentioned above, the fluid sample held in the reactor well 105 reacts with the chemically sensitive layer 201, thereby changing the refractive index, $n_l$, of the chemically sensitive layer 201. Further, the light energy propagating around the ring waveguide resonator 106 causes an evanescent wave field 302 to be produced that reaches out into the chemically sensitive layer 201. This causes the refractive index, $n_m$, and the resonant frequency, $f_{m0}$, of the ring waveguide resonator 106 (also called the measuring arm) to change.

Similarly, the fluid sample held in the reactor well 104 and exposed to the ring waveguide resonator 108 causes the refractive index, $n_r$, and the resonant frequency, $f_{r0}$, of the ring waveguide resonator 108 (also called the reference arm) to change. Further, because the refractive indices, $n_m$ and $n_r$, change, the light beams propagating through the ring waveguide resonators 106 and 108 undergo phase shifts. As a result, chemical and biological substances in the fluid samples held in the reactor wells 104 and 105 can be detected by the detectors 204 and 206 by measuring relative changes in the resonant frequencies, $f_{m0}$ and $f_{r0}$, of the ring waveguide resonators 106 and 108.

The operation of the MEOMS sensing chip 100 will now be described in accordance with the following illustrative example. First, the micro-fluidic delivery system (not shown) transports fluid samples (not shown) through the inlet channels 107 and 109 to the reactor wells 104 and 105, respectively. It is assumed that the fluid samples held in the reactor wells 104 and 105 include the same types of chemical or biological substances; however, the quantities of the substances in the fluid samples may or may not be the same. Further, it is assumed in this example that the surfaces of the measuring arm, i.e., the ring waveguide resonator 106, and the reference arm, i.e. the ring waveguide resonator 108, do not interface with the chemically sensitive layer 201. Accordingly, in this illustrative example, the MEOMS sensing chip 100 will be used for performing differential measurements of the chemical or biological substances in the fluid samples exposed to the ring waveguide resonators 106 and 108.

Next, the laser 202 injects a coherent light beam into the input portion 112 of the channel waveguide 110, thereby preferably causing the coherent light beam to propagate as a single mode within the channel waveguide 110. This is because it is desired that essentially all of the light energy associated with the coherent light beam be evanescently coupled into the ring waveguide resonators 106 and 108 when the light frequency equals the resonant frequencies, $f_{m0}$ and $f_{r0}$. If the coherent light beam were to propagate within the channel waveguide 110 as more than one mode, then it is expected that not all of the light energy associated with all of the modes will be evanescently coupled into the ring waveguide resonators 106 and 108 at resonance.

As mentioned above, the channel waveguide 110 is fabricated so that approximately 50% of the light energy of the injected light beam propagates within the measurement branch 116 and the remaining 50% of the light energy propagates within the reference branch 114. Further, the light beam propagating within the measurement branch 116 is evanescently coupled into the ring waveguide resonator 106, thereby causing light energy to propagate around the ring waveguide resonator 106 in a clockwise manner. Similarly, the light beam propagating within the reference branch 114 is evanescently coupled into the ring waveguide resonator 108, thereby causing light energy to propagate around the ring waveguide resonator 108 in a counter clockwise manner. At the resonant frequencies, $f_{m0}$ and $f_{r0}$, of the ring waveguide resonators 106 and 108, the intensities, $I_{m0}$ and $I_{r0}$, of the light beams coupled out of the measurement and the reference branches 116 and 114 will fall to minimum values.

In this illustrative example, the input current to the laser 202, which is preferably a laser diode, is varied by a ramp signal produced by the servo 210, thereby causing the light frequency of the injected light beam to sweep through a range of frequencies sufficiently wide enough to encompass the resonant frequencies, $f_{m0}$ and $f_{r0}$, of the ring waveguide resonators 106 and 108. This approach is especially useful when the phase shift induced in the light energy propagating around the ring waveguide resonators 106 and 108 is large; e.g., from $0.1\pi$ to $2\pi$ radians.

Figure 5A:
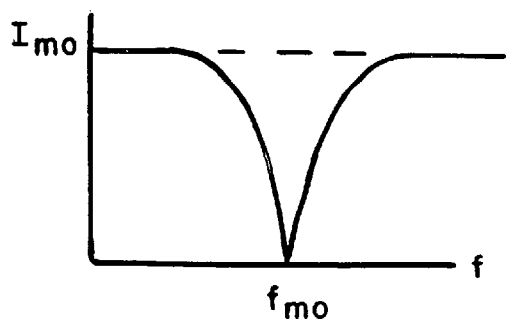
FIGS. 5A and 5B are graphical representations of the intensities of light coupled out of the optical sensing chip module with respect to the light frequency.

For example, FIG. 5A shows the intensity, $I_{m0}$, of the light beam coupled out of the measurement branch 116 and provided to the detector 204, versus the swept light frequency, f, of the injected light beam. Further, the fluid sample exposed to the ring waveguide resonator 106 causes the resonant frequency of the measuring arm to be equal to $f_{m0}$. Accordingly, the intensity, $I_{m0}$, falls to a minimum at the frequency, $f_{m0}$, because essentially all of the light energy of the light beam propagating through the measurement branch 116 is evanescently coupled into the ring waveguide resonator 106.

Figure 5B:
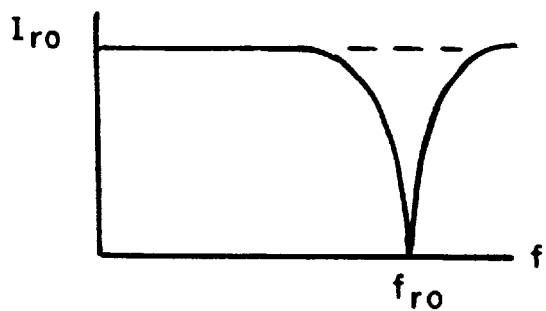

Similarly, FIG. 5B shows the intensity, $I_{r0}$, of the light beam coupled out of the reference branch 114 and provided to the detector 206, versus the swept light frequency, f, of the injected light beam. Further, the fluid sample exposed to the ring waveguide resonator 108 causes the resonant frequency of the reference arm to be equal to $f_{r0}$. Accordingly, the intensity, $I_{r0}$, falls to a minimum at the frequency, $f_{r0}$, because essentially all of the light energy of the light beam propagating through the reference branch 114 is evanescently coupled into the ring waveguide resonator 108.

As a result, a differential measurement of the chemical and biological substances in the fluid samples exposed to the ring waveguide resonators 106 and 108 can be made by comparing the relative resonant frequencies, $f_{m0}$ and $f_{r0}$, of the ring waveguide resonators 106 and 108.

When the phase shift induced in the light energy propagating around the ring waveguide resonators 106 and 108 is small, e.g., on the order of $10^{-5}\pi$ radians, then a different detection approach is useful. Specifically, the processor 208 monitors the intensity, $I_{r0}$, of the light detected by the detector 206 and uses the servo 210 to set the input current of the laser 202 so that the frequency of the light energy produced by the laser 202 is at the resonant frequency, $f_{r0}$, of the ring waveguide resonator 108. Next, the induced phase shift is determined using synchronous modulation/demodulation.

Figure 6A:
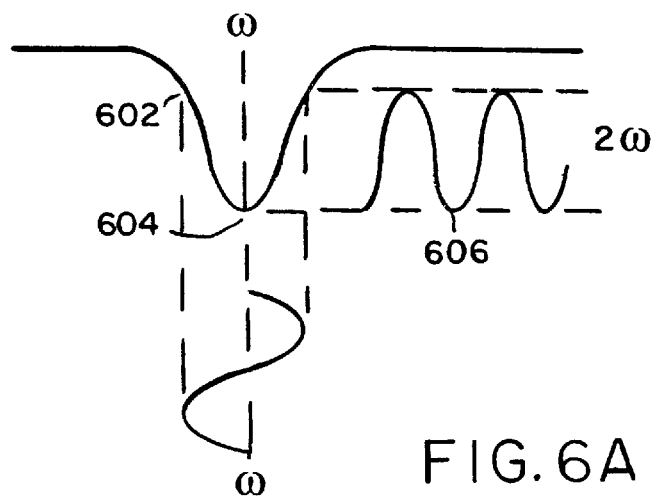
FIG. 6A is a graphical representation of the modulated beam coincident with the resonant frequency of the reference arm and of the corresponding detector output.

For example, FIG. 6A shows that when the light frequency 602 of the laser 202 is coincident with the resonant frequency 604, i.e., $\omega_{r0}=2\pi f_{r0}$, of the ring waveguide resonator 108, the modulation is centered on the minimum of the resonance dip. The output signal 606 of the detector 206 due to the modulation across the resonant frequency 604 is therefore a pure sinusoid at twice the modulation frequency, which for this example is equal to 20 kHz. Accordingly, when the processor 208 demodulates the output signal 606 at the modulation frequency, zero signal results.

Figure 6B:
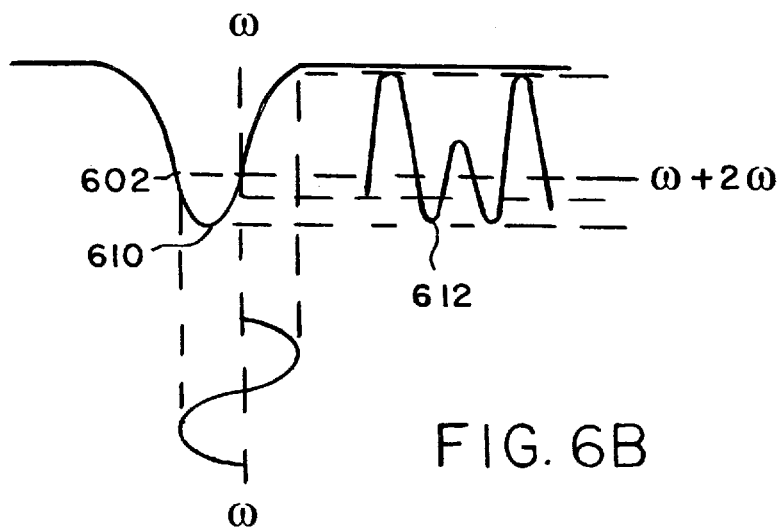
FIG. 6B is a graphical representation of the modulated beam not coincident with the resonant frequency of the measuring arm and of the corresponding detector output.

Further, FIG. 6B shows that when the light frequency 602 is offset from the resonant frequency 610, i.e., $\omega_{m0}=2f_{m0}$, of the ring waveguide resonator 106, the output signal 612 from the detector 204 picks up oscillations at the modulation frequency. Accordingly, when the processor 208 demodulates the output signal 612 at the modulation frequency, a dc signal results. As a result, a differential measurement of the chemical and biological substances in the fluid samples exposed to the ring waveguide resonators 106 and 108 can be made by determining the magnitude of the resulting dc signal.

Having described one embodiment, numerous alternative embodiments or variations might be made. For example, it was described that the MEOMS sensing chip includes a plurality of ring waveguide resonators, each ring waveguide resonator having a respective reactor well aligned with a portion thereof. However, this was merely an illustration. The MEOMS sensing chip may alternatively include a reactor well that is large enough to be aligned with portions of both the ring waveguide resonator comprising the measuring arm and the ring waveguide resonator comprising the reference arm. This structure is particularly useful for eliminating the effects of biochemical and environmental factors such as non-specific binding and temperature variation in the fluid sample held in the large reactor well.

For example, the surface of the measuring arm may interface with a chemically sensitive layer, thereby allowing it to respond to both specific and non-specific interactions in the fluid sample. Further, because the surface of the reference arm does not interface with the chemically sensitive layer, the reference arm will respond to only non-specific interactions in the fluid sample. As a result, all non-specific interactions are concealed by differentiating the outputs of the measuring and the reference arms, thereby allowing the MEOMS sensing chip to detect only specific binding in the fluid sample.

Figure 7:
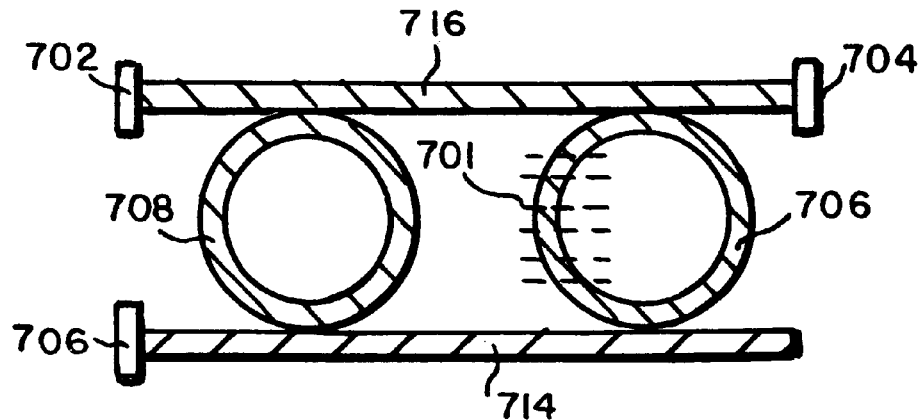
FIG. 7 is a schematic view of an alternate embodiment of the optical sensing chip module in accordance with the present invention.

It was also described that the MEOMS sensing chip includes a two-branch channel waveguide. However, this was also merely an illustration. FIG. 7 shows that the MEOMS sensing chip may alternatively include a laser 702 that injects a light beam into a channel waveguide 716. The light beam is evanescently coupled into both the ring waveguide resonator 706 (the measuring arm) and the ring waveguide resonator 708 (the reference arm), thereby causing light energy to propagate around the ring waveguide resonators 706 and 708 in a clockwise manner. The light energies in the ring waveguide resonators 706 and 708 are then evanescently coupled into the channel waveguide 714. If the laser 702 is controlled for sweeping the light frequency of the injected beam through a range of frequencies sufficiently wide enough to encompass the resonant-frequencies of the ring waveguide resonators 706 and 708, then the detectors 704 and 706 can be used for determining these resonant frequency values. As a result, a differential measurement of the chemical and biological substances in the fluid samples exposed to the ring waveguide resonators 706 and 708 can be made by comparing the relative resonant frequencies, $f_{m0}$, and $f_{r0}$, of the ring waveguide resonators 706 and 708.

Figure 8:
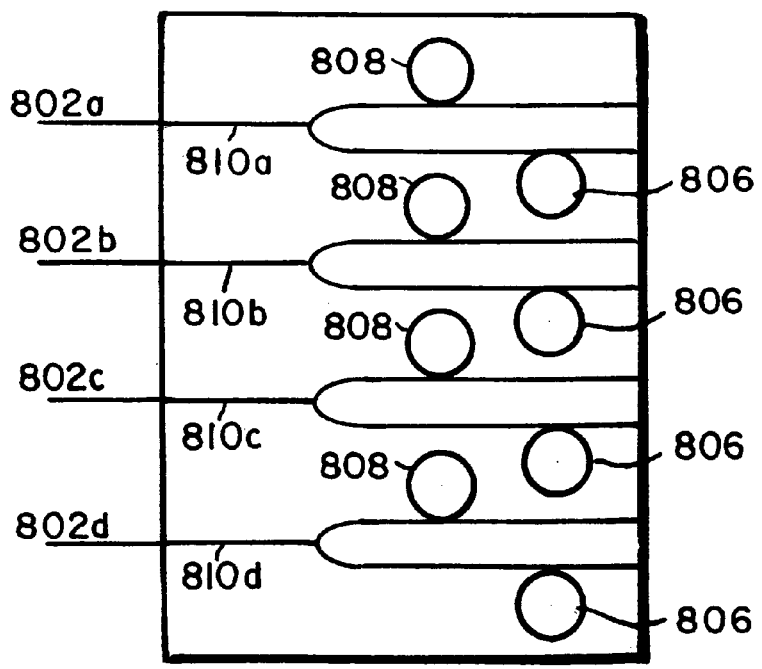
FIG. 8 is a plan view of the bottom surface of the MEOMS sensing chip showing an alternate embodiment of the optical sensing chip module in accordance with the present invention.

In addition, FIG. 8 shows an alternative optical sensing chip module 822 with an array of two-branch waveguides 810a, 810b, 810c, and 810d, each having corresponding measuring arms 806, reference arms 808, and lasers 802a, 802b, 802c, and 802d.

Because fluid samples in reactor wells (not shown) aligned with the measuring arms 806 react independently with chemically sensitive layers (not shown) interfacing with portions of the measuring arms 806, the optical sensing chip module 822 can be used for performing simultaneous detection and measurement of a plurality of chemical and biological substances in fluid samples.

It was also described that each micro-channel includes an inlet channel and an outlet channel for transporting fluid samples into and out of a respective reactor well. However, this was merely an illustration. Inlet channels of a plurality of micro-channels may alternatively merge together for mixing a plurality of samples and then transporting the mixed samples to a reactor well.

All documents mentioned herein are specifically incorporated herein by reference.

The invention has been described in detail, including the preferred embodiments thereof. However, it will be appreciated that those skilled in the art, upon consideration of the present disclosure, may make modification and/or improvements of this invention and will be within the scope and spirit of the invention as set forth in the following claims.

What is claimed is:

1. A device for optically sensing substances in fluid samples, comprising:
   a first channel waveguide for coupling light energy into a first ring waveguide, the first ring waveguide having a test sample applied to a surface thereof;
   a chemically sensitive layer interfaced with the first ring waveguide, the test sample reacting with the chemically sensitive layer to change a refractive index of the chemically sensitive layer, wherein the light energy propagating around the first ring waveguide produces an evanescent wave field which causes a change in resonant frequency of the first ring waveguide;
   a second channel waveguide for coupling light energy in to a second ring waveguide, the second ring waveguide having a reference sample applied to a surface thereof;
   a laser for injecting light into the first and the second channel waveguides; and
   at least one detector for measuring the intensities of light coupled out of the first and the second channel waveguides,
   wherein the intensity measurements are used for sensing substances in the test sample relative to the reference sample.

2. The device as recited in claim 1,
   wherein the light injected by the laser is coherent.

3. The device as recited in claim 2,
   wherein the coherent light propagates within the first and the second channel waveguides as a single mode.

4. A method for optically sensing substances in fluid samples, comprising:
   interfacing a chemically sensitive layer with a first ring waveguide;
   exposing a test sample to the first ring waveguide, the test sample reacting with the chemically sensitive layer to change a refractive index of the chemically sensitive layer;
   injecting a light beam into a first channel waveguide, thereby coupling at least a portion of the light beam energy into the first ring waveguide, wherein the light energy propagating around the first ring waveguide produces an evanescent wave field which causes a change in resonant frequency of the first ring waveguide; and
   detecting the intensity of a remaining portion of the light beam energy coupled out of the first channel waveguide,
   wherein the detected energy is indicative of the presence of a substance in the test sample.

5. The method as recited in claim 4,
   wherein the step of exposing includes contacting the test sample to a surface of the first ring waveguide.

6. The method as recited in claim 4,
   wherein the step of injecting includes varying the light frequency through a range of frequencies that includes the resonant frequency of the first ring waveguide.

7. The method as recited in claim 6,
   wherein the resonant frequency of the first ring waveguide is dependent upon substances in the test sample exposed thereto.

8. The method as recited in claim 6,
   wherein the detected intensity approaches a minimum value as the light frequency approaches the resonant frequency of the first ring waveguide.

9. The method as recited in claim 4,
   wherein the step of exposing further includes exposing a reference sample to a second ring waveguide, and
   wherein the step of injecting includes injecting bifurcated light beams into the first channel waveguide and a second channel waveguide, thereby coupling at least a portion of the bifurcated light beam energies into the first and the second ring waveguides.

10. The method as recited in claim 9,
    wherein the step of detecting includes detecting the intensities of remaining portions of the bifurcated light beam energies coupled out of the first and the second channel waveguides.

11. The method as recited in claim 10,
    wherein the detected intensities approach minimum values as the light frequency approaches the resonant frequencies of the first and the second ring waveguides.

* * * * *